United States Patent
Karasawa (10) Patent No.: US 6,969,620 B2
(45) Date of Patent: Nov. 29, 2005

(54) SEMICONDUCTOR DEVICE INSPECTION SYSTEM

(75) Inventor: Wataru Karasawa, Tokyo (JP)

(73) Assignee: Tokyo Electron Limited, Tokyo (JP)

( * ) Notice: Subject to any disclaimer, the term of this patent is extended or adjusted under 35 U.S.C. 154(b) by 137 days.

(21) Appl. No.: 10/258,444

(22) PCT Filed: Apr. 24, 2001

(86) PCT No.: PCT/JP01/03525

§ 371 (c)(1), (2), (4) Date: Feb. 6, 2003

(87) PCT Pub. No.: WO01/82364

PCT Pub. Date: Nov. 1, 2001

(65) Prior Publication Data

US 2003/0155280 A1 Aug. 21, 2003

(30) Foreign Application Priority Data

Apr. 25, 2000 (JP) .......................... 2000-124875

(51) Int. Cl.[7] .......................... H01L 21/66; G01R 31/26
(52) U.S. Cl. .................. 438/14; 324/158.1; 700/121
(58) Field of Search .................. 438/14; 324/158.1; 700/121; 364/468.28

(56) References Cited

U.S. PATENT DOCUMENTS

| 5,210,041 A | | 5/1993 | Kobayashi et al. |
| 5,219,765 A | | 6/1993 | Yoshida et al. |
| 5,654,632 A | * | 8/1997 | Ohno ........................ 324/158.1 |
| 5,940,300 A | * | 8/1999 | Ozaki .......................... 700/121 |
| 6,055,463 A | * | 4/2000 | Cheong et al. ............. 700/223 |

FOREIGN PATENT DOCUMENTS

| JP | 7-302819 | 11/1995 |
| JP | 11-330184 | 11/1999 |
| WO | 00/14790 | 3/2000 |

\* cited by examiner

Primary Examiner—W. David Coleman
(74) Attorney, Agent, or Firm—Crowell & Moring LLP (57) ABSTRACT

A device inspection apparatus inspects a plurality of semiconductor devices on an individual device basis. An inspection target sorting part (8) omits an execution of an inspection to be applied to the semiconductor devices according to information which specifies a defective device that has been determined to be defective in a manufacturing process that has been applied to the device.

15 Claims, 5 Drawing Sheets

SEMICONDUCTOR DEVICE INSPECTION SYSTEM

TECHNICAL FIELD

The present invention relates to an inspection apparatus and, more particularly, to an inspection apparatus and system for inspecting semiconductor devices.

BACKGROUND ART

In a manufacturing process of a semiconductor integrated circuit, after completion of a process, the result of the process is investigated. At this time, a thickness of a film deposited on a wafer, on which a semiconductor integrated circuit is formed, is measured by an inspection apparatus different from the manufacturing apparatus that carried out the process. Additionally, a particle inspection may also be conducted. Thereby, a check of a process is performed. That is, when fault is found in an inspected object by such check, it is determined that a certain defect exists in the manufacturing apparatus and the manufacturing apparatus is fixed. In addition, since productivity would fall if all wafers are subjected to the inspection, only a wafer extracted by arbitrary samplings is inspected.

In recent years, the above-mentioned inspection apparatus has been built into the inside of the manufacturing apparatus, which carries out the process. Thereby, the manufacturing apparatus, which can inspect all wafers without reducing productivity, has also been developed. In the manufacture apparatus of such a type, since an inspecting unit is built therein, a detection result is fed back to the manufacturing apparatus shortly after a defective part is detected in the manufactured wafer so as to take measures of automatically changing process conditions.

However, a thickness of the film formed on the wafer may vary on an individual wafer basis, or also vary within each wafer. In process conditions, such as temperature and pressure, an instability based on unevenness due to the change with passage of time and difference in position etc. There may be a case in which a defective part is not detected due to the instability, or a degree of defectiveness is small. In such a case, the manufacturing process is continued without changing process conditions.

In a final probe inspection process that is performed after completion of the manufacturing processes, the semiconductor integrated circuits formed on the wafer are subjected to an electric function test so as to judge whether the semiconductor integrated circuits are good in their quality.

Therefore, even when it is judged by the prove inspection in the last process stage as mentioned above that the semiconductor integrated circuit is defective, the probe inspection is conducted to all the chips in which the semiconductor integrated circuits are formed. Accordingly, the-probe inspection is performed on the defective semiconductor integrated circuit, which is not adopted as a product. Thus, there is a problem in that the probe inspection is unnecessarily performed on the defective semiconductor integrated circuit.

DISCLOSURE OF INVENTION

It is a general object of the present invention to provide an improved and useful device inspection apparatus in which the above-mentioned problems are eliminated.

A more specific object of the present invention is to provide a device inspection apparatus and method of inspecting a semiconductor device in which the semiconductor device can be efficiently inspected so as to improve productivity and cost performance thereof.

In order to achieve the above-mentioned objects, there is provided according to one-aspect of the present invention a device inspection apparatus for inspecting a plurality of devices on an individual device basis, characterized in that: an inspection target sorting part omits an execution of an inspection to be applied to the devices according to information which specifies a defective device that has been determined to be defective in a manufacturing process that has been applied to the device.

According to the above-mentioned invention, the inspection to be applied to a defective device is omissible by the inspection target sorting part, thereby reducing a time spent on the inspection performed after the devices are completed.

The device inspection apparatus according to the present invention may further comprise a marking part which provides a mark to one of the devices of which inspection is omitted by the inspection target sorting part. Accordingly, the defective device can be easily recognized by the mark.

Additionally, in the device inspection apparatus according to the present invention, the information which specifies a defective device may be stored in a memory part. Accordingly, the information can be used at an appropriate time if necessary, thereby achieving reliable devices without defective devices.

Additionally, there is provided according to another aspect of the present invention a device manufacturing system comprising: a device manufacturing apparatus which manufactures a plurality of devices and acquires information which specifies a device having a defective part; and a device inspection apparatus which inspects the devices manufactured by the device manufacturing apparatus, characterized in that: the device inspection apparatus includes an inspection target sorting part which omits an execution of an inspection to be applied to the devices according to the information which specifies a device having a defective portion that has been formed during a manufacturing process performed by the device manufacturing apparatus.

According to the above-mentioned invention, the inspection to be applied to a defective device is omissible by the inspection target sorting part, thereby reducing a time spent on the inspection performed after the devices are completed.

Further, there is provided according to another aspect of the present invention a device manufacturing system comprising: a plurality of device manufacturing apparatuses; and an inspection apparatus which inspects the devices manufactured by manufacturing processes performed by said device manufacturing apparatuses, characterized in that: an inspection part performs an inspection to determine whether a defect occurs in the devices during the manufacturing processes of the devices after the devices are subjected to the manufacturing process by at least two of the device manufacturing apparatuses, and acquiring information specifying one of the devices determined to be defective; and the inspection apparatus includes an inspection target sorting part which omits an execution of an inspection to be applied to the devices according to the information which specifies a defective device that has been determined to be defective in the manufacturing processes of the device.

According to the above-mentioned invention, the inspection to be applied to a defective device is omissible by the inspection target sorting part, thereby reducing a time spent on the inspection performed after the devices are completed.

Additionally, there is provided according to another aspect of the present invention a device inspection method for inspecting a plurality of devices on an individual device basis, characterized by the steps of: preparing information which specifies a defective device determined to be defective in a manufacturing process of said devices; and omitting an execution of an inspection to be applied to one of said devices determined to be defective in accordance with the information prepared in the preparing step. The device inspection method may further comprise a step of providing a mark to said one of the devices of which inspection is omitted. Additionally, The device inspection method may further comprise a step of storing the information prepared in the preparing step in a memory.

Other objects, features and advantages of the present invention will become more apparent from the following detailed description when read in conjunction with the accompanying drawings.

BEST MODE FOR CARRYING OUT THE INVENTION

A description will be given, with reference to the drawings, of embodiments of the present invention. In the following description, although manufacture of a semiconductor integrated circuit is explained as an example, the present invention is not restricted to a manufacture of a semiconductor integrated circuit, but can be widely applied to a manufacture of a device containing a liquid-crystal display panel etc.

Figure 1:
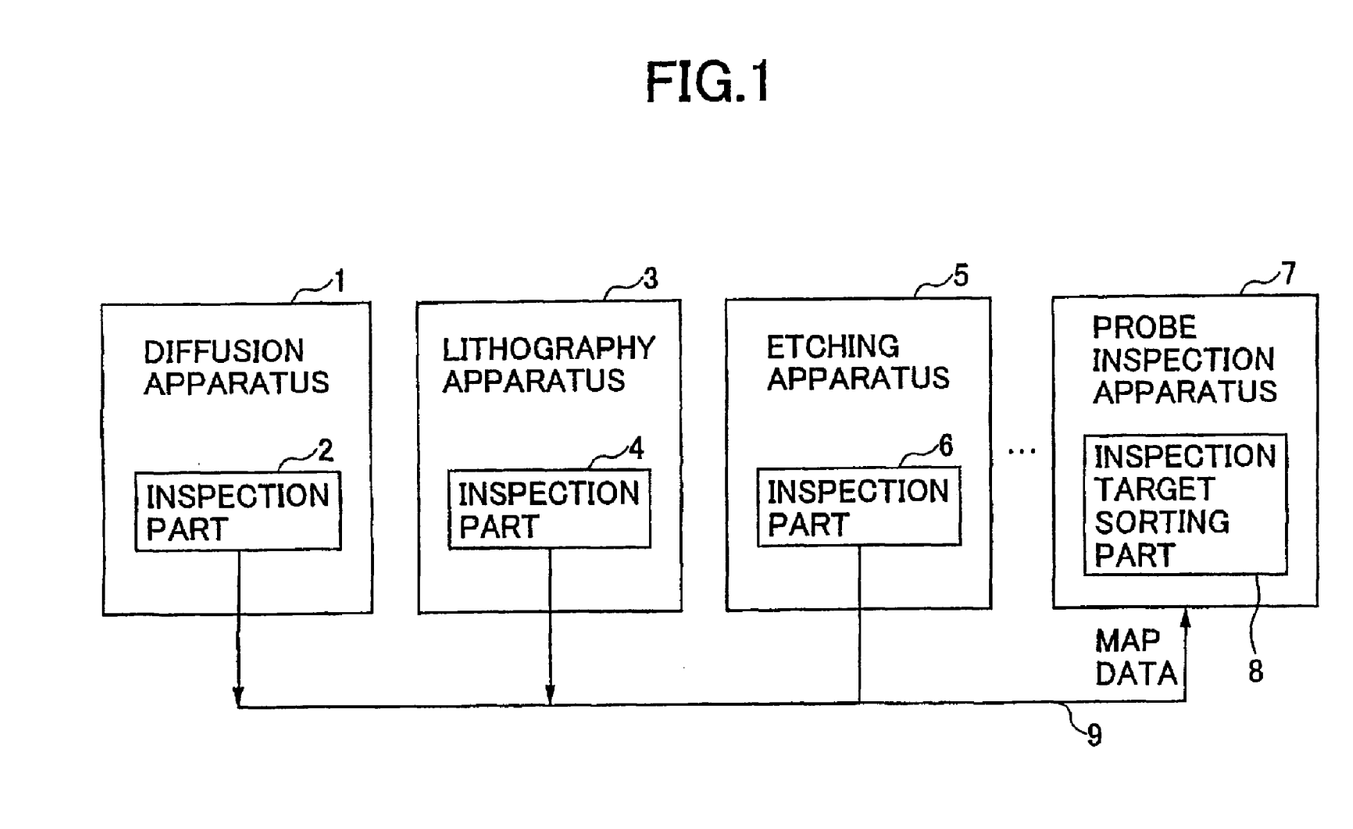
FIG. 1 is a block diagram showing an outline structure of a semiconductor integrated circuit manufacturing system according to a first embodiment of the present invention.

FIG. 1 is a block diagram showing an outline structure of a semiconductor integrated circuit manufacturing system according to a first embodiment of the present invention. As shown in FIG. 1, the semiconductor integrated circuit manufacturing system according to the first embodiment of the present invention comprises: a plurality of apparatuses used in a manufacturing process of semiconductor integrated circuits, such as a diffusion apparatus 1, a lithography apparatus 3, and an etching apparatus 5; a probe inspection apparatus 7 which inspects the semiconductor integrated circuits manufactured through the manufacturing process on an individual chip basis; and a communication line 9 which interconnects these apparatuses.

In the above-mentioned diffusion apparatus 1, a diffusion process by ion implantation is applied to a wafer on which semiconductor integrated circuits are formed. Additionally, in the lithography apparatus 3, a pattern formation is performed by printing and developing a predetermined pattern after applying a sensitization agent on a surface of the wafer and exposing through a photograph mask. Further, in the etching apparatus 5, an etching process is performed such as selective removal of an oxidization film. In the probe inspection apparatus 7, a probe is brought into contact with electrodes formed in the chip on an individual chip basis formed on the wafer so as to perform a connection test of the circuit formed in the chips.

As shown in FIG. 1, inspection parts 2, 4 and 6 are incorporated into the diffusion apparatus 1, the lithography apparatus 3 and the etching apparatus 5, respectively. An inspection target sorting part 8 is built in the probe inspection apparatus 7. The inspection parts 2, 4, and 6 and the inspection target sorting part 8 are connected by the communication line 9.

A description will now be given of an outline of an operation of the semiconductor integrated circuit manufacturing system having the above-mentioned structure. First, each of the inspection parts 2, 4, and 6 shown in FIG. 1 inspects whether a wafer, which passed through each manufacturing process, has a defect on an individual wafer basis. That is, for example, the inspection part 6 built in the etching apparatus 5 measures a thickness of the wafer to which a predetermined etching was applied in the etching apparatus 5, and inspects whether the thickness of the wafer falls within an allowable range with respect to a design value. If the measured thickness is not within the allowable range, it is determined that the wafer is defective.

At this time, each of the inspection parts 2, 4, and 6 specifies a position on the wafer determined to be a defective part by the inspection conducted by each of the inspection parts 2, 4 and 6, and supplies information (for example, map data, such as position coordinates data) which specifies the position through the communication line 9 to the inspection target sorting part 8 of the probe inspection apparatus 7.

Thereby, the inspection target sorting part 8 excludes the chip containing the portion judged to be defective by one of the inspection part 2, 4, and 6 from the target objects to be subjected to the probe inspection according to the supplied information. Accordingly, since the probe inspection is omissible about the chip that is determined to be a defective product, a time spent on a useless inspection can be omitted and the probe inspection time can be reduced.

It should be noted that although the information which specifies the defective chip is explained as what is supplied to the inspection target sorting part 8 from the inspection parts 2, 4, and 6 through the communication line 9, it is not necessary to use the communication line 9. For example, the information acquired in each of the inspection parts 2, 4, and 6 can be recorded on a recording medium such as a floppy disk or a CD-ROM. Then, the recording medium may be attached to the probe inspection apparatus 7 so as to supply the information recorded on the recording medium to the inspection target sorting part 8.

Figure 2:
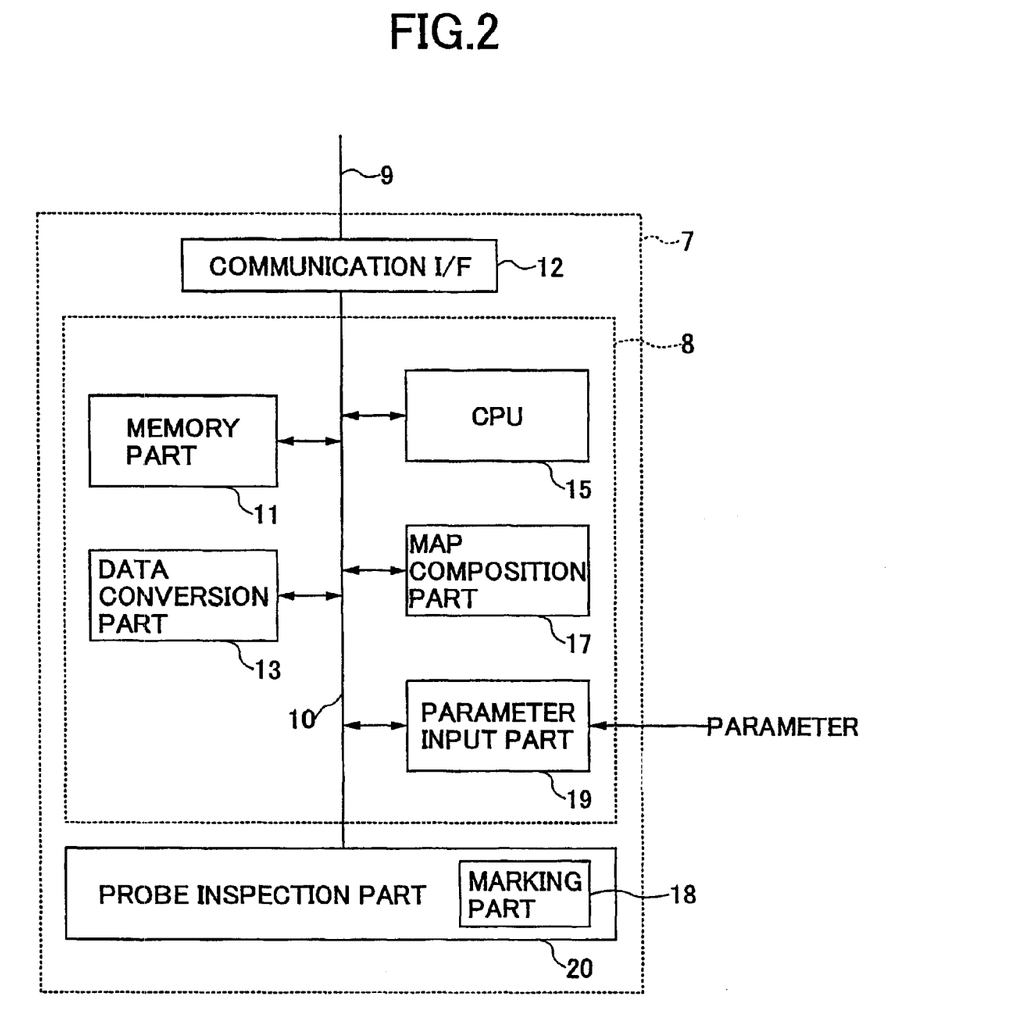
FIG. 2 is a block diagram showing a structure of a probe inspection apparatus shown in FIG. 1.

A description will now be given of the semiconductor integrated circuit manufacturing system shown in FIG. 1 in detail. FIG. 2 is a block diagram showing a structure of the probe inspection apparatus 7 shown in FIG. 1. As shown in FIG. 2, the probe inspection apparatus 7 comprises the inspection target sorting part 8, a marking part 18, and a probe inspection part 20. The inspection target sorting part 8 includes a bus 10, a memory part 11, a data conversion part 13, a central processing unit (CPU) 15, a map composition part 17, and a parameter input part 19. The memory part 11, the data conversion part 13, the CPU 15, the map composition part 17, the marking part 18, the parameter input part 19 and the probe inspection part 20 are connected to the bus 10. The bus is connected to the communication line 9 shown in FIG. 1 via a communication interface 12.

Figure 3:
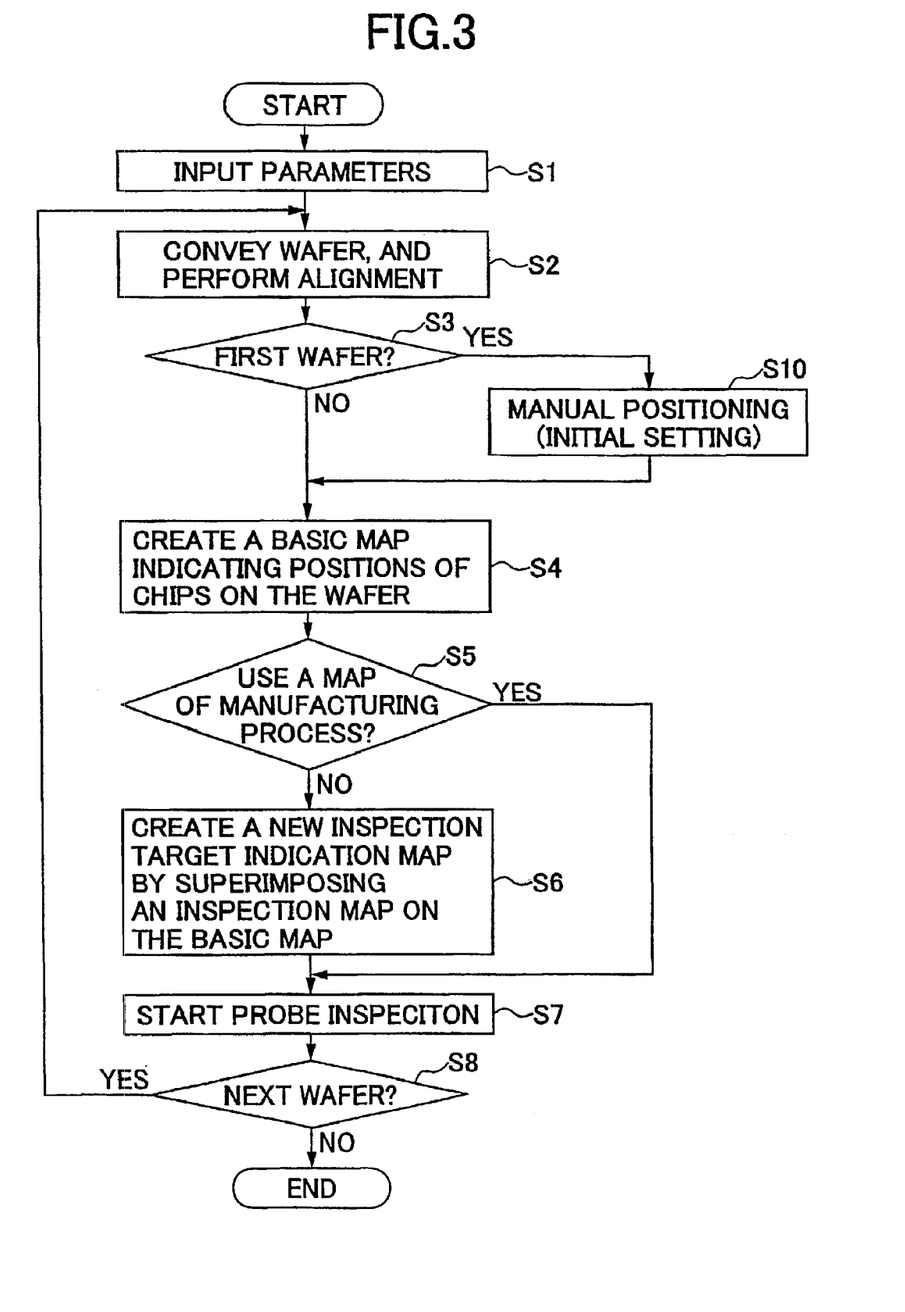
FIG. 3 is a flow chart of an operation of the probe inspection apparatus shown in FIG. 2.

A description will now be given, with reference to FIG. 3, of an operation of the probe inspection apparatus 7. First, when a power is supplied to the semiconductor integrated circuit manufacturing system, the CPU 15 sends a command which request the input of the parameter by the user to the parameter input part 19. Then, as shown in step S1 of FIG. 3, the user inputs various parameters to the parameter input part 19. For example, the parameters contains information regarding a size of the wafer, a size of each chip formed on the wafer and an orientation of the original flat (notch) which is a mark for specifying the position of the chips formed on the wafer.

Then, in step S2, the probe inspection part 20 conveys the wafer, which is an object to be tested, to a predetermined position, and performs positioning of the wafer on the basis of the original flat formed on the wafer. It should be noted that an X-Y stage controlled by the interferometer is used in the position operation. After pre-alignment in made to roughly position the wafer, precise alignment is performed.

Thereafter, in step S3, the CPU 15 determines whether the wafer conveyed in Step S2 is the first one of the wafers to be inspected. If it is determined that the wafer is the first one, the routine proceeds to step S10. On the other hand, when it is determined that the wafer is not the first one, the routine proceeds to step S4.

That is, in the first test, a chuck on which the wafer containing chips is put is moved manually so as to perform a positioning so that a probe of the probe inspection part 20 is connected to an electrode of the chip to be tested. It should be noted that the initial setting is necessary only at once since the positioning of the second one and subsequent to the second one can be automatically performed based on the position information obtained through the initial setting and stored in the memory part 11.

Next, in step S4, the positions of the chips that exist at the end of the four directions of the wafer, to which the probe inspection part 20 applies a test, are measured. The map composition part 17 creates a basic map, which indicates the position of the chip set as an object to be subjected to the probe inspection according to the position information acquired by the measurement.

On the other hand, the CPU 15 stores in the memory part 11 the position information of the chip which has been determined to be defective according to the result of the inspection by each of the inspection parts 2, 4, and 6 shown in FIG. 1, and causes the map composition part 17 create an inspection map which indicates the position of a chip determined to be defective by the inspection in the preceding process based on the position information.

Figure 4:
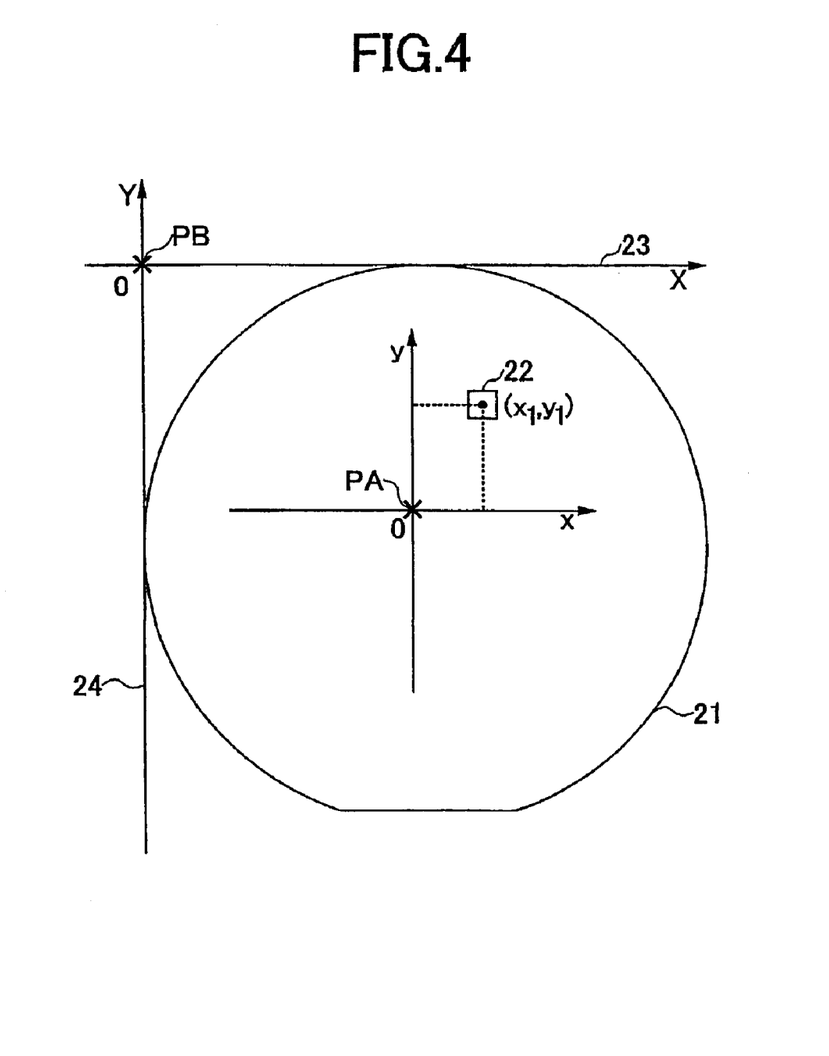
FIG. 4 is an illustration for explaining a data conversion performed by the probe inspection apparatus shown in FIG. 2.

A description will now be given of the creation of the inspection map. Each of the inspection parts 2, 4, and 6 shown in FIG. 1 measures the position on the wafer of the portion determined to be defective, and acquires the position information regarding the portion. At this time, an x-y (or X-Y) coordinate system as shown in FIG. 4 is used. The x-y (or X-Y) coordinate system has the origin of coordinates corresponding to the central point PA of a wafer 21 or the intersection PB of the tangential lines 23 and 24 of the wafer 21. As shown in FIG. 4, in the x-y coordinate system that has the origin of coordinates corresponding to the central point PA of the wafer, coordinates ($x_1$, $y_1$) are acquired as position information of a chip 22.

Then, the position information which is acquired by each of the inspection parts 2, 4, and 6 is supplied to the memory part 11 through the communication line 9 as map data. At this time, information specifying the coordinate system used as a standard in creating the position information is supplied to the memory part 11 together with the position information.

Then, if it is determined that the coordinate system made into the above-mentioned standard indicated in the information supplied by the inspection parts 2, 4, and 6 differs from each other, the CPU 15 issues an instruction to perform coordinates conversion to the data conversion part 13 so that all position information is expressed in one of the coordinate systems.

Thereby, the data conversion part 13 performs coordinate conversion by primary conversion or the like. The thus-acquired position information is stored in the memory part 11, and is also supplied to the map composition part 17. Then, the CPU 15 causes the map composition part 17 create the inspection map which indicates the position of the portion determined to be defective by the inspection of the previous process based on the position information. It should be noted that, the thus-created inspection map is stored in the memory part 11.

Next, it is determined in step S5 whether the inspection map should be taken into consideration when a determination is made to select the chip as an object to be subjected to the probe inspection. The determination of the use of the inspection map is made by the user in response to a request by the CPU 15. If the user instructs to take the inspection map into consideration through a keyboard input or the like, the routine proceeds to step S6. Otherwise, the routine proceeds to step S7.

In step S6, with directions of CPU15, the map composition part 17 superimposes the inspection map created in Step S4 on a basic map so as to create a new inspection target indication map. The new inspection target indication map indicates only the position of the chip other than the chips containing a portion determined as defective at the previous processes among all the chips on the wafer made into the object to be subjected to the probe inspection. The inspection target indication map is also stored in the memory part 11.

Next, in step S7, the probe inspection part 20 carries out probe inspection one by one only about the chip of which position is clearly indicated on the inspection target indication map. Then, when the probe inspection is completed for all the chips indicated on the inspection target indication map, the routine proceeds to step S8. In step S8, the CPU 15 determines whether or not a subsequent wafer to be subjected to the probe inspection is present. If it is determined that there is the subsequent wafer, the routine proceeds to step S2. On the other hand, if it is determined that there is no subsequent wafer, the routine is ended.

It should be noted that a mark may be given to the chips which are determined to be defective by the prove inspection so as to package the chips which are not give the mark in the subsequent process. Additionally, the mark may be given to the chips determined to contain a defective portion in the previous process such as the process performed by the diffusion apparatus 1, the lithography apparatus 3 or etching apparatus 5 before the probe inspection is performed. Namely, if a user inputs a command which instruct to perform marking according to the inspection in the previous process, the CPU 15 reads the inspection map stored in the memory part 11 so as to supply the inspection map to the marking part 18. Then, the marking part 18 provides a mark one by one to the chips containing the defective portion indicated on the supplied inspection map.

Accordingly, since the chips which do not have the mark can be distinguished easily as a good product when picking up the chips, a reliable semiconductor integrated circuit can be positively manufactured.

Additionally, since the inspection map, which indicates the position of a chip determined to be defective by the inspection of the previous process, is stored in the memory part, it is useful to record the inspection map on a recording media such as a floppy disk or a CD-ROM. The recording medium can be attached to a pickup apparatus which picks up a chip so as to supply the inspection map to the pickup apparatus. Alternatively, the inspection map may be supplied to the pickup apparatus through a communication lined. That is, if the chips indicated on the inspection map as containing the defective portion is prevented from being picked up by the pickup apparatus, an unnecessary pick up operation can be omitted which results in an improvement of the manufacturing efficiency of the semiconductor integrated circuit.

Furthermore, the diffusion apparatus 1, the lithography apparatus 3, the etching apparatus 5 and the probe inspection apparatus 7 shown in FIG. 1 may constitute a single wafer processing system built in one conveyance system. According to such a system, a wafer is sequentially supplied to the apparatuses provided in the system while being automatically carried in and out of the apparatuses so as to apply processes and inspections to the wafer. Thus, the time required for the probe inspection is reduced, and, thereby, the efficiency of the probe inspection is improved and the manufacture system of the semiconductor integrated circuit having a high-productivity can be achieved.

Figure 5:
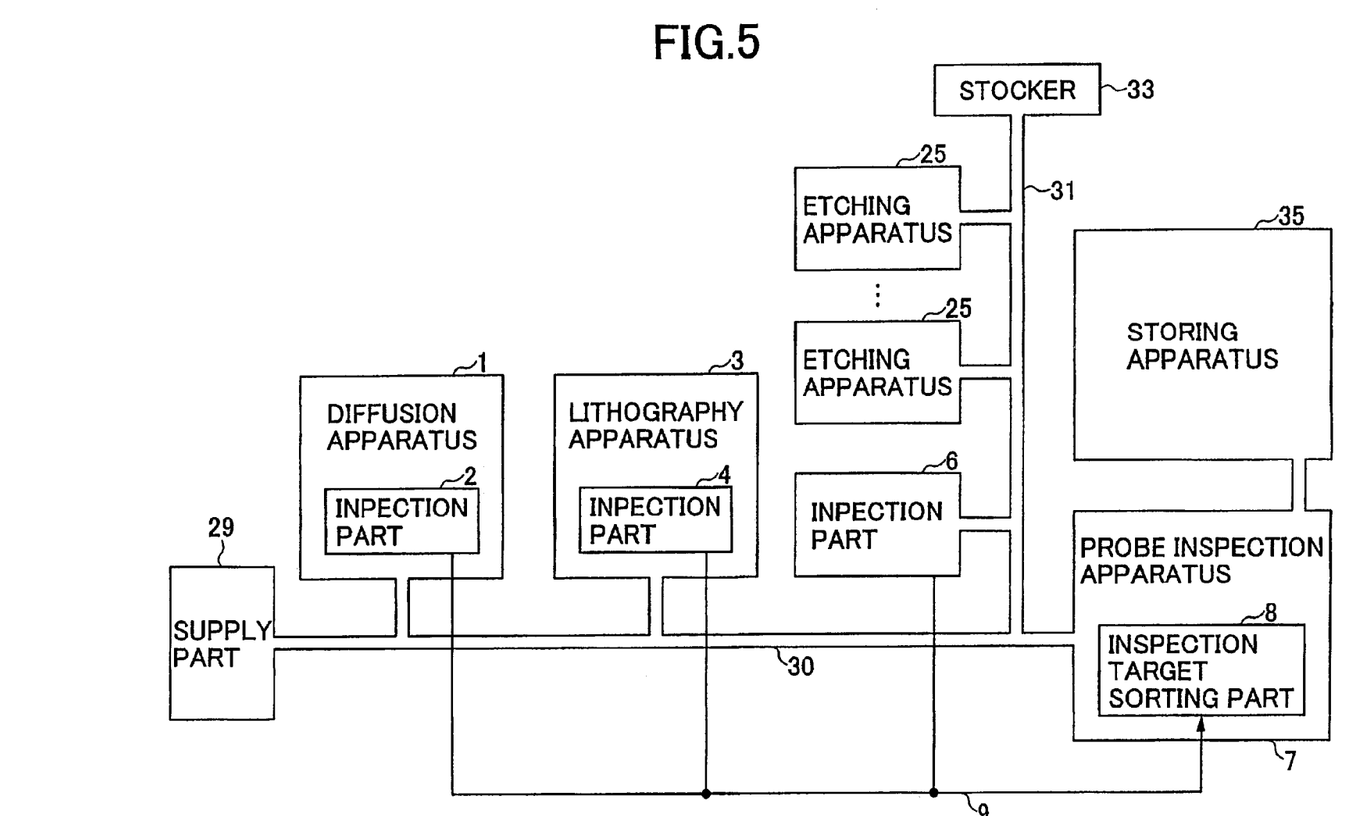
FIG. 5 is a block diagram of an outline structure of a semiconductor integrated circuit manufacturing system according to a second embodiment of the present invention.

A description will now be given, with reference to FIG. 5, of a semiconductor integrated circuit manufacturing system according to a second embodiment of the present invention. FIG. 5 is a block diagram of an outline structure of the semiconductor integrated circuit manufacturing system according to the second embodiment of the present invention. As shown in FIG. 5, although the semiconductor integrated circuit manufacturing system according to the second embodiment of the present invention has the same composition as the semiconductor integrated circuit manufacturing system according to the first embodiment of the present invention shown in FIG. 1, they differ from each other in that the semiconductor integrated circuit manufacturing system according to the second embodiment is provided with a single wafer conveyance system which conveys one wafer at a time. The single wafer conveyance system comprises a supply part 29, conveyance paths 30 and 31, a stocker 33 and a storing apparatus 35.

Additionally, as shown in FIG. 5, a plurality of etching apparatuses 25 which do not have an inspection part therein are arranged in parallel along the conveyance path 31. Further, an independent inspection part 6 is provided along the same conveyance path 31 in the row of the etching apparatuses.

It should be noted that the above-mentioned supply part 29 is connected to an end of the conveyance path 30, and the stocker 33 is connected to an end of the conveyance path 31. The storing apparatus 35 is connected to the probe inspection apparatus 7.

Since the operation of the semiconductor integrated circuit manufacturing system according to the second embodiment of the present invention basically the same as that of the semiconductor integrated circuit manufacturing system according to the first embodiment shown in FIG. 1, a description will be given below of the differences therebetween.

First, wafers supplied to the supply part 29 are conveyed along the conveyance path 30 to the diffusion apparatus 1 one by one so as to apply a diffusion process to each wafer in the diffusion apparatus 1. Then, an inspection is performed so as to determine whether there is a portion in which defective diffusion has occurred. If there is a portion judged that the defect has occurred, the position information on the defective portion is acquired and the position information is supplied to the inspection target sorting part 8 through the communication line 9.

Then, the wafer to which the diffusion process has been applied is conveyed to the lithography apparatus 3, and the wafer is patterned in the lithography apparatus 3. Then, an inspection is performed by the inspection part 4 so as to determine whether there is a portion in which a defective pattern has been produced. If it is determined that there is a defective pattern, the position information of the defective portion is acquired and the position information is supplied to the inspection target sorting part 8 through the communication line 9.

Next, the patterned wafer is conveyed along the conveyance path 31 to the etching apparatus 25, and an etching process is performed in the etching apparatus 25. Then, the etched wafer is conveyed to the inspection part 6, and an inspection is performed by the inspection part 6 so as to determine whether there is a defective etched portion. If there is a defective etched portion, the position information on the defective etched portion is acquired and the position information is supplied to the inspection target sorting part 8 through the communication line 9. At this time, a plurality of wafers can be concurrently subjected to the etching process by the plurality of etching apparatuses 25 arranged along the conveyance path 31. Additionally, in order to adjust the processing speed with that of other manufacturing processes, the etched wafer can be temporarily stored in the stocker 33.

The wafer inspected by the inspection part 6 is conveyed to a subsequent processing apparatus (not shown) along the conveyance path 30 again, and the predetermined processes are sequentially performed. Thus, the processed wafer is conveyed to the probe inspection apparatus 7, and the probe inspection explained in detail in the first embodiment is applied to the wafer. It should be noted that the wafer, which passed through the probe inspection, is conveyed and stored in the storing apparatus 35 so as to be subjected to a subsequent process.

Additionally, in the above-mentioned structure, the supply part 29, the stocker 33 and the storing apparatus 35 are not necessarily separated from each other. For example, the supply part 29 may have the function of the stocker 33 or the storing apparatus 35.

As mentioned above, according to the semiconductor integrated circuit manufacturing system according to the present invention, since the inspection part 6 is provided to the plurality of etching apparatuses 25, it is not necessary to provide an inspection part in each of the etching apparatuses 25. Therefore, the cost of the etching apparatus 25 is reduced, which result in reduction in the cost of the whole semiconductor integrated circuit manufacturing system. Additionally, although a total non-operating time of the whole inspection parts is increased in a case in which the inspection part is provided to each of the processing apparatuses, the cost performance can be improved by providing the inspection part 6 common to a plurality of processing apparatuses.

It should be noted that although the structure in which only the etching apparatuses 25 are arranged in parallel was explained in the second embodiment of the present invention, other apparatuses such as cleaning apparatuses or chemical vapor deposition (CVD) apparatuses may be arranged in parallel. Additionally, the same effect as the semiconductor integrated circuit manufacturing system shown in FIG. 5 can be achieved by providing a plurality of inspection parts shared by the plurality of processing apparatus arranged in parallel.

The present invention is not limited to the specifically disclosed embodiments, and variations and modifications may be made without departing from the scope of the present invention.

What is claimed is:

1. A device inspection apparatus for inspecting a plurality of devices on an individual device basis comprising:
    an inspection target sorting part which omits an execution of an inspection to be applied to one of the devices according to information which specifies said one of the devices as being a defective device, the information being acquired by an inspection of said one of the devices during manufacturing of said one of the devices.

2. The device inspection apparatus as claimed in claim 1, wherein a marking part provides a mark to one of said devices of which inspection is omitted by said inspection target sorting part.

3. The device inspection apparatus as claimed in claim 1, wherein the information which specifies a defective device is stored in a memory part.

4. A device manufacturing system comprising:
    a device manufacturing apparatus which manufactures a plurality of devices and acquires information which specifies a device having a defective part; and
    a device inspection apparatus which inspects the devices manufactured by said device manufacturing apparatus, wherein:
    said device inspection apparatus includes an inspection target sorting part which omits an execution of an inspection to be applied to one of the devices according to the information which specifies said one of the devices as being a device having a defective portion that has been formed during manufacturing by said device manufacturing apparatus the information being acquired by an inspection applied to said one of the devices during manufacturing of said one of the devices.

5. The device manufacturing system as claimed in claim 4, wherein a marking part provides a mark to one of said devices of which inspection is omitted by said inspection target sorting part.

6. The device inspection apparatus as claimed in claim 4, wherein the information which specifies a defective device is stored in a memory part.

7. A device manufacturing system comprising:
    a plurality of device manufacturing apparatuses; and
    an inspection apparatus which inspects the devices manufactured by said device manufacturing apparatuses, wherein:
    an inspection part performs an inspection to determine whether a defect occurs in the devices during the manufacturing of the devices after the devices are manufactured by at least two of said device manufacturing apparatuses, and acquiring information specifying one of the devices determined to be defective; and
    said inspection apparatus includes an inspection target sorting part which omits an execution of an inspection to be applied to said one of the devices according to the information which specifies said one of the devices as being a defective device the information being acquired by an inspection applied to said one of the devices during manufacturing of said one of the devices.

8. A device inspection method for inspecting a plurality of devices on an individual device basis, comprising:
    preparing information which specifies a defective device determined to be defective during manufacturing of said devices; and
    omitting an execution of an inspection to be applied to one of said devices determined to be defective in accordance with the information prepared in the preparing step.

9. The device inspection method as claimed in claim 8, further including providing a mark to said one of the devices of which inspection is omitted.

10. The device inspection method as claimed in claim 8, further including storing the information prepared in the preparing step in a memory.

11. An inspection apparatus for inspecting a plurality of devices on an individual device basis, said arrangement comprising:
    an inspection target sorting device including input means for receiving information indicating a defective state of each of said plurality of devices and an output means providing a defective device output signal specifying ones of said plurality of devices which are indicated as defective; and
    a device inspection system receiving said defective device output signal and providing inspection of only ones of said plurality of devices which are not indicated as defective by said defective output signal.

12. A device inspection apparatus for inspecting a plurality of devices on an individual device basis comprising:
    an inspection target sorting part which omits an execution of an inspection to be applied to the devices according to information which specifies a defective device that has been determined to be defective in a manufacturing process that has been applied to the device, wherein a marking part provides a mark to one of said devices of which inspection is omitted by said inspection target sorting part.

13. A device manufacturing system comprising:
    a device manufacturing apparatus which manufactures a plurality of devices and acquires information which specifies a device having a defective part; and
    a device inspection apparatus which inspects the devices manufactured by said device manufacturing apparatus, wherein:
    said device inspection apparatus includes an inspection target sorting part which omits an execution of an inspection to be applied to the devices according to the information which specifies a device having a defective portion that has been formed during a manufacturing process performed by said device manufacturing apparatus; and
    a marking part provides a mark to one of said devices of which inspection is omitted by said inspection target sorting part.

14. A device inspection method for inspecting a plurality of devices on an individual device basis, comprising:
    preparing information which specifies a defective device determined to be defective in a manufacturing process of said devices;
    omitting an execution of an inspection to be applied to one of said devices determined to be defective in accordance with the information prepared in the preparing step; and providing a mark to said one of the devices of which inspection is omitted.

15. An inspection apparatus for inspecting a plurality of devices on an individual device basis, said arrangement comprising:

an inspection target sorting device including an input which receives information indicating a defective state of each of said plurality of devices and an output which provides a defective device output signal specifying ones of said plurality of devices which are indicated as defective; and a device inspection system receiving said defective device output signal and providing inspection of only ones of said plurality of devices which are not indicated as defective by said defective output signal.

* * * * *